S005152823A

United States Patent [19]

Albrecht et al.

[11] Patent Number: 5,152,823
[45] Date of Patent: Oct. 6, 1992

[54] LIQUID HERBICIDAL MIXED FORMULATIONS

[75] Inventors: Konrad Albrecht, Kelkheim; Gerhard Frisch, Wehrheim, both of Fed. Rep. of Germany

[73] Assignee: Hoechst Aktiengesellschaft, Frankfurt am Main, Fed. Rep. of Germany

[21] Appl. No.: 641,068

[22] Filed: Jan. 14, 1991

Related U.S. Application Data

[63] Continuation of Ser. No. 203,946, Jun. 8, 1988, abandoned.

[30] Foreign Application Priority Data

Jun. 10, 1987 [DE] Fed. Rep. of Germany ..... 37192647

[51] Int. Cl.$^5$ ............................................ A01N 57/00
[52] U.S. Cl. ............................................ 71/79; 71/86; 71/92; 71/93; 71/109; 71/119; 71/DIG. 1
[58] Field of Search ................. 71/79, 86, DIG. 1, 92, 71/93, 119, 109

[56] References Cited

U.S. PATENT DOCUMENTS

| | | | |
|---|---|---|---|
| 3,933,460 | 1/1976 | Fischer | 71/DIG. 1 |
| 4,400,196 | 8/1983 | Albrecht et al. | 71/86 |
| 4,549,027 | 10/1985 | Gates | 71/92 |
| 4,626,274 | 12/1986 | Hausmann et al. | 71/93 |
| 4,640,905 | 2/1987 | Gabe et al. | 71/93 |
| 4,748,202 | 5/1988 | Ball et al. | 524/823 |
| 4,804,399 | 2/1989 | Albrecht et al. | 71/93 |

FOREIGN PATENT DOCUMENTS 0130370 1/1985 European Pat. Off.
3238958 3/1984 Fed. Rep. of Germany.

Primary Examiner—C. Warren Ivy
Assistant Examiner—Raymond Covington
Attorney, Agent, or Firm—Curtis, Morris & Safford

[57] ABSTRACT

Aqueous pesticidal agents based on active substance-containing dispersions in combination with water-soluble active substances, which agents contain at least 3 active substances, at least 2 of which are present in the disperse form and at least 1 of which is water-soluble, and contain alkyl ether sulfates combined with ethoxylated fatty alcohols and sulfosuccinic monoesters as surfactants, have a broad range of applications and advantageous properties in use.

5 Claims, No Drawings

LIQUID HERBICIDAL MIXED FORMULATIONS

This application is a continuation of application Ser. No. 203,946, filed Jun. 8, 1988, now abandoned.

DESCRIPTION

The present invention relates to novel formulations of plant protecting agents based on aqueous, active substance-containing dispersions in combination with water-soluble active substances of plant protecting agents.

Formulations of aqueous dispersions containing one active substance in the solid, disperse phase and another in the form of an aqueous solution, such as, for example, isoproturon and herbicides of the phenoxy series (EP-A 0,130,370), have been disclosed.

In these formulations, the range of applications, which is determined to a great extent by the number of the active substances contained, is limited.

Surprisingly, it has now been found that, on using a certain mixture of surfactants, it is possible to prepare combined formulations which can contain two or more active substances in the disperse phase and, in addition, salt-like, water-soluble active substances. Due to this increase of possibilities to combine active substances, the ready-mix formulations according to the invention are distinguished by a very broad range of applications.

Thus, the present invention is directed to aqueous-based herbicidal agents, which contain a specific mixture of surfactants and more than two active substances, in particular three active substances, of which at least two active substances are present in disperse form and at least one active substance is water-soluble.

The solid, disperse active substances of plant protecting agents include, for example, triazines, such as simazine, atrazine and cyanazine; phenylurea derivatives, such as, for example, isoproturon, chlortoluron, linuron, monolinuron and diuron; substituted pyridines, such as 3,5,6-trichloro-2-pyridyloxacetate (I) or 4-amino-3,5-dichloro6-fluoro -pyridyloxacetate (II), ioxinyl and bromoxinyl; diphenyl ethers, such as, for example, oxifluorfen, triphenyltin and tributyltin compounds in the form of the acetate or hydroxide, carbendazim; endosulfan; deltamethrin; and compounds from the group of the triazoles and imidazoles.

Examples of water-soluble active substances which may be mentioned are the salts of phosphinothricin, such as glufosinate; glyphosate and its salts; paraquat; herbicides of the phenoxy series, such as chloromethyl-phenoxypropionic acid (CMPP), 2,4-dichlorophenoxyacetic acid, 2,4-dichlorophenoxypropionic acid, methylchlorophenoxy- and acetic acid (MCPA); and also dimethylphosphinoylhydroxyacetic acid or their salts, 3-isopropyl-(1H)-benzo-2,1,3-benzo-thiadiazin-4-one 2,2-dioxide and 1,1-dimethyl-4,4'-dichloride. Salts which can be used are all salts which can be employed in agriculture. These include preferably alkali metal salts and alkaline earth metal salts, or monosubstituted, disubstituted or trisubstituted ammonium salts. The substituents on the nitrogen atom in the latter can be independently of one another identical or different. In particular, they denote ($C_1$-$C_{14}$)-alkyl (optionally branched), hydroxyalkyl or ($C_1$-$C_{14}$)-alkanoyl.

Optically active compounds can be employed as the pure isomers or as mixtures of enantiomers.

Almost all of the abovementioned active substances of plant protecting agents are described in "The Pesticide Manual", 7th Ed., British Crop Protection Council (1983). Dimethylphosphinoylhydroxyacetic acid has been disclosed in DE-OS 3,238,958.

The surfactant mixture according to the invention, permitting the combination of one, but mainly two or more solid active substances to be dispersed with at least one or more water-soluble active substances to give a liquid ready-mix formulation on an aqueous base, is composed of alkyl ether sulfates, combined with ethoxylated fatty alcohols and sulfosuccinic monoesters.

In this context, the alkyl ether sulfates are taken to mean those having a chain length of $C_{10}$–$C_{18}$, especially lauryl, and an ethoxyation degree of 1-5 EO units, especially 2-3 EO units, in the form of their alkali metal, alkaline earth metal or ammonium salts, it being possible for the latter to be substituted as described above. ®Genapol LRO is a specific example of an alkyl ether sulfate surfactant of Hoechst AG.

Suitable ethoxylated fatty alcohols are alcohols having a chain length of $C_8$-$C_{20}$, especially $C_{13}$ on average, and an ethoxylation degree of 5-30 EO units, especially 5-13 EO, as they are commercially available, for example, under the name ®Genapol of Hoechst AG x-series.

The sulfosuccinic monoester alkali metal salt used in this process (HOE S 1728) is described in German Patent No. 2,132,405. It is prepared by reacting a polyglycol ether of a condensation product of a monooctyl- or mononoyl-phenol and formaldehyde at a molar ratio of alkylphenol to formaldehyde of 2:1 to 10:9, which polyglycol ether contains 2 to 8 moles of alkylene oxide units per mole of alkylphenol, with maleic anhydride and an alkali metal sulfite.

In order to increase the viscosity, organic or inorganic thickeners, such as those based on xanthane derivatives or alumosilicates, can also be added to the surfactant mixture. These ready-mix formulations prepared on the basis of the surfactant mixture described can additionally contain defoamers, for example on a silicone base, and also antifreeze on an urea or polyol base.

In general, the surfactant mixture is composed of 0.2-20% by weight, preferably 0.5-15%, of alkyl ether sulfate, 0.1-6% by weight, preferably 0.1-3%, of ethoxylated fatty alcohol, and 1-20% by weight of sulfosuccinic monoester alkali metal salt. The ready-mix formulation can additionally contain 1-70% by weight of active substances. The ratio of the active substances in the finely-disperse phase to the active substances dissolved in water is determined by the biological type of action, but it can be between 100:1 and 1:100, preferably, however, between 20:1 and 1:20.

The formulations according to the invention can be prepared in various manners. On the one hand, a procedure can be followed such that the individual ingredients are prepared in the form of individual dispersions and solutions, which are then mixed by means of a colloid mill. Alternatively, it is possible to grind the active substances of the finely-disperse phase together and to add the solution of active substances to this mixed dispersion as described above. In principle, it is also possible for all the active substances to be processed in one run to give the desired mixed formulation. The two processes mentioned last may present problems concerning the uniformity of the particles of the finely disperse active substances, as these active substances may have different grinding properties.

The combined formulations prepared in this manner have good storability, exhibit virtually no chemical changes and are easy to handle when applied.

Of course, it is also possible to use the surfactant combination described here in systems in which only one active substance is present in the finely-disperse phase and one active substance is present in the solution.

Examples which are meant to illustrate the process according to the invention in more detail are listed in the table below:

| Composition [% by weight] | Example No. | | | | | | | | | | | | | | | | | | | | | | | |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| Alkyl ether sulfate | 12 | 13 | 1 | 1 | 0,5 | 15 | 10 | 11 | 8 | 8 | 12 | 7 | 8 | 2 | 12 | 10 | 13 | 11 | 10 | 7 | 20 | 10 | 5 | 8 |
| Ethoxylated fatty alcohol | 0,5 | 0,5 | 0,5 | 0,5 | 1 | 0,5 | 0,5 | 0,5 | 0,5 | 0,5 | 0,5 | 2,0 | 0,7 | 0,7 | 0,5 | 0,5 | 0,5 | 0,5 | 0,5 | 0,7 | 3 | 0,8 | 0,9 | 0,7 |
| HOE S 1728 | 13 | 11 | 12 | 13 | 17 | 10 | 13 | 13 | 10 | 11 | 14 | 14 | 10 | 15 | 7 | 7 | 11 | 10 | 12 | 10 | 5 | 12 | 12 | 10 |
| Diuron | 17 | 15 | 16 | 15 | 21 | | 17 | 17 | 20 | | 16 | 8 | 2 | 10 | 30 | | 15 | 15 | 14,5 | 3 | | 15 | 21 | 14 |
| Chlortoluron | | | | | | | | | | 6 | | | | | | | | | | | | | | |
| Isoproturon | | | | | | | | | 5 | | | | | | | | | | | | | | | |
| Atrazine | | | | | | 10 | | | | | | | | | | | | | | | | | | |
| Cyanazine | | | | | | | | 11 | | | | | | | | | | | | | | | | |
| Simazine | 11 | 10 | 11 | 11 | 15 | 8 | | | | 15 | 10 | 20 | 15 | 15 | | 26 | 10 | | | 15 | | 10 | 15 | 10 |
| Glyphosate | | | | | | | | | | | 8 | 6 | | | | | | | | | | | | |
| III | | | | | | | | | | | | | | | | | 8 | | | | | | | |
| MCPA | | | | | | | | | | | | | 11,5 | 12 | | | | | | | | | | |
| Monolinuron | | | | | 15 | | | | | | | | | | | | | | | 5 | | | | |
| I | | | | | | | | | | | | | | | | | | 4 | | | | | | |
| II | | | | | | | | | | | | | | | | | | | 4 | | | | | |
| CMPP | | | | | | | | | | | | | | | | | | | | 11,5 | | | | |
| Linuron | | | | | | | | | | | | | | | | | | | | | 20 | | | |
| Glufosinate | 9 | 8 | 8,5 | 11 | 13 | 11 | 9 | 9 | 10 | 8 | | | 7,5 | | 8 | 7 | | 8 | 8,5 | 7 | 15 | 12 | 13 | 7 |
| Water to 100% | | | | | | | | | | | | | | | | | | | | | | | | |

I = 3,5,6-trichloro-2-pyridyloxyacetate
II = 4-amino-3,5-dichloro-6-fluoro-2-pyridyloxyacetate
III = dimethylphosphinoylhydroxyacetic acid

We claim:

1. An aqueous herbicidal formulation comprising:
at least two active substances in dispersed form, at least one active substance which is water-soluble and wherein the active substances are present in the amount of 1–70% by weight of the formulation; and
a surfactant consisting of an admixture of 7 to 12% by weight of alkyl ether sulfate, 0.5 to 2.0% by weight of ethoxylated fatty alcohol and about 14% by weight of sulfosuccinic monoester alkali metal salt.

2. An aqueous herbicidal formulation comprising at least two active substances in dispersed form and one active substance which is water-soluble, wherein the active substances are selected from the group consisting of diuron, chlorotoluron, isoproturon, atrazine, cyanazine, simazine, linuron, monolinuron, glyphosate, glufosinate, dimethylphosphinoylhydroxy-acetic acid, 2,4-dichlorophenoxyacetic acid, 2,4- dichlorophenoxypropionic acid, methylchlorophenoxyacetic acid and chloromethylphenoxypropionic acid or agriculturally suitable salts thereof, and wherein said active substances are present in the amount of 8 to 20% by weight; and
a surfactant consisting of an admixture of 7 to 12% by weight of an alkyl ether sulfate, 0.5 to 2.0% by weight of ehtoxylated fatty alcohol and about 14% by weight of sulfosuccinic monoester alkali metal salt.

3. The formulation as claimed in claim 2, which contains, as active substances, 6 to 8% by weight of glufosinate, 10 to 20% by weight of simazine, 8 to 16% by weight of diuron; and
a surfactant consisting of an admixture of 7 to 12% by weight of alkyl ether sulfate, 0.5 to 2.0% by weight of ethoxylated fatty alcohol, and about 14% by weight sulfosuccinic monoester alkali metal salt.

4. The formulation as claimed in claim 2, which contains, as active substances, 8% by weight of glufosinate, 10% by weight of simazine, 16% by weight of diuron; and
a surfactant consisting of an admixture of 12% by weight of alkyl ether sulfate, 0.5% by weight of ethoxylated fatty alcohol, and 14% by weight sulfosuccinic monoester alkali metal salt.

5. The formulation as claimed in claim 2, which contains, as active substances, 6% by weight of glufosinate, 20% by weight of simazine, 8% by weight of diuron; and
a surfactant consisting of an admixture of 7% by weight of alkyl ether sulfate, 2.0% by weight of ethoxylated fatty alcohol, and 14% by weight sulfosuccinic monoester alkali metal salt.

* * * * *